United States Patent [19]

Aller et al.

[11] 4,259,330
[45] Mar. 31, 1981

[54] NEMATOCIDAL PHOSPHORAMIDATES

[75] Inventors: Harold E. Aller, Norristown; Edward E. Kilbourn, Chalfont; Ernest D. Weiler, Ambler; William D. Weir, Levittown, all of Pa.

[73] Assignee: Rohm and Haas Company, Philadelphia, Pa.

[21] Appl. No.: 662,751

[22] Filed: Mar. 1, 1976

[51] Int. Cl.³ .................. A01N 57/28; A01N 57/32
[52] U.S. Cl. .................. 424/200; 260/429 R; 260/429.7; 260/429.9; 260/438.1; 260/439 R; 260/938; 260/939; 260/941; 260/959; 260/958; 424/211; 544/64; 544/157; 544/337; 546/11; 546/22; 546/24
[58] Field of Search ............. 260/247.1 B, 293.85, 260/938; 424/200, 212, 211

[56] References Cited

U.S. PATENT DOCUMENTS

| | | | |
|---|---|---|---|
| Re. 30,240 | 3/1980 | Aller et al. | 424/211 |
| 3,384,683 | 5/1968 | Schwarze | 260/938 |
| 3,393,253 | 7/1968 | Wiesboeck et al. | 260/938 |
| 3,476,837 | 11/1969 | Addor et al. | 260/959 |
| 3,887,657 | 6/1975 | Battershell et al. | 260/938 |
| 3,887,657 | 6/1975 | Battershell | 260/938 |
| 3,957,924 | 5/1976 | Meyer et al. | 424/211 X |
| 3,975,522 | 8/1976 | Bader | 260/293.85 X |
| 4,076,809 | 2/1978 | Weir et al. | 424/211 |
| 4,139,614 | 2/1979 | Kilbourn et al. | 424/200 X |

FOREIGN PATENT DOCUMENTS

| | | | |
|---|---|---|---|
| 952712 | 11/1956 | Fed. Rep. of Germany | 260/938 |
| 1139494 | 11/1962 | Fed. Rep. of Germany | 260/938 |
| 2114885 | 12/1972 | Fed. Rep. of Germany | 260/938 |
| 2260710 | 6/1974 | Fed. Rep. of Germany | 260/938 |
| 2805682 | 8/1978 | Fed. Rep. of Germany | 424/211 |
| 39-18119 | 8/1964 | Japan | 260/938 |
| 7216946 | 6/1973 | Netherlands . | |
| 1048314 | 5/1965 | United Kingdom | 260/938 |
| 216712 | 7/1968 | U.S.S.R. | 260/938 |

OTHER PUBLICATIONS

Migrdichian, V., et al., *Organic Synthesis*, vol. 1, Reinhold Publishing Corp., New York, 1957, pp. 405–407.
Derwent Japanese Patent Reports, vol. 6, No. 10, 4/19/67.
Migrdichian, V., et al., *Organic Synthesis*, vol. 1, Reinhold Publishing Corp., New York, 1957, pp. 405–407.

*Primary Examiner*—Richard A. Schwartz
*Attorney, Agent, or Firm*—Bernard J. Burns

[57] ABSTRACT

This invention relates to novel phosphoramidates of the formula:

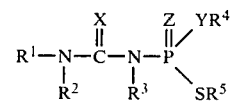

wherein
$R^1$ is hydrogen, alkyl, cycloalkyl, or optionally substituted aralkyl, aryl, pyridyl, pyridylmethyl, pyridylethyl or pyrazinyl;
$R^2$ is hydrogen provided $R^1$ is other than optionally substituted aryl; alkyl; cycloalkyl; alkoxyalkyl; alkylthioalkyl; cyanoalkyl; alkenyl; optionally substituted aralylky; or optionally substituted aryl, provided $R^1$ is other than hydrogen;
$R^1$ and $R^2$ taken together with the nitrogen to which they are attached form an optionally substituted morpholino or piperidino group;
$R^3$ is hydrogen, alkyl, cycloalkyl, alkenyl, or optionally substituted aralkyl or aryl;
$R^4$ is ($C_1$-$C_6$) alkyl;
$R^5$ is ($C_3$-$C_4$) alkyl; and X, Y and Z are independently oxygen or sulfur;

the agronomically acceptable metal salts and metal salt complexes thereof; and to methods of using them to control nematodes.

3 Claims, No Drawings

NEMATOCIDAL PHOSPHORAMIDATES

This invention relates to novel phosphoramidates, to compositions containing them and to method of using them to control nematodes.

The novel compounds of this invention can be represented by the formula:

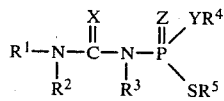  (I)

wherein $R^1$ is
(a) a hydrogen atom;
(b) a ($C_1$-$C_{12}$) alkyl group, preferably a ($C_1$-$C_8$) alkyl group;
(c) a ($C_3$-$C_8$) cycloalkyl group, preferably a ($C_5$-$C_7$) cycloalkyl group;
(d) an optionally substituted aralkyl group of up to 11 carbon atoms, preferably an optionally substituted benzyl or phenethyl group;
(e) an optionally substituted ($C_6$-$C_{10}$) aryl group, preferably an optionally substituted phenyl group;
(f) an optionally substituted pyridyl group;
(g) an optionally substituted pyridylmethyl or pyridylethyl group; or
(h) an optionally substituted pyrazinyl group;

$R^2$ is
(a) a hydrogen atom, provided $R^1$ is other than an optionally substituted ($C_6$-$C_{10}$) aryl group;
(b) a ($C_1$-$C_{10}$) alkyl group, preferably a ($C_1$-$C_6$) alkyl group;
(c) a ($C_3$-$C_8$) cycloalkyl group, preferably a ($C_5$-$C_7$) cycloalkyl group;
(d) a ($C_2$-$C_{10}$) alkoxyalkyl group, preferably a ($C_2$-$C_6$) alkoxyalkyl group;
(e) a ($C_2$-$C_{10}$) alkylthioalkyl group, preferably a ($C_2$-$C_6$) alkylthioalkyl group;
(f) a ($C_1$-$C_6$) cyanoalkyl group;
(g) a ($C_3$-$C_6$) alkenyl group, preferably a ($C_3$-$C_4$) alkenyl group;
(h) an optionally substituted aralkyl group of up to 11 carbon atoms, preferably an unsubstituted benzyl or phenethyl group;
(i) an optionally substituted ($C_6$-$C_{10}$) aryl group, provided $R^1$ is other than hydrogen, preferably an unsubstituted phenyl group;

$R^1$ and $R^2$ taken together with the nitrogen atom to which they are attached form a morpholino or piperidino group, optionally substituted with up to two ($C_1$-$C_4$) alkyl, preferably methyl, groups;

$R_3$ is
(a) a hydrogen atom;
(b) a ($C_1$-$C_{10}$) alkyl group, preferably a ($C_1$-$C_6$) alkyl group;
(c) a ($C_3$-$C_8$) cycloalkyl group, preferably a ($C_5$-$C_7$) cycloalkyl group;
(d) a ($C_3$-$C_6$) alkenyl group, preferably a ($C_3$-$C_4$) alkenyl group;
(e) an optionally substituted aralkyl group of up to 11 carbon atoms, preferably an unsubstituted benzyl or phenethyl group; or
(f) an optionally substituted ($C_6$-$C_{10}$) aryl group, preferably an unsubstituted phenyl group;

$R^4$ is a ($C_1$-$C_6$) alkyl group, preferably a ($C_1$-$C_4$) alkyl group;
$R^5$ is a ($C_3$-$C_4$) alkyl group;
X is an oxygen or sulfur atom;
Y is an oxygen or sulfur atom, preferably an oxygen atom; and
Z is an oxygen or sulfur atom, preferably an oxygen atom;
and the agronomically acceptable metal salts and metal salt complexes thereof.

The metal salts of this invention are the alkali and alkaline earth metal salts of the compounds of Formula I wherein at least one of $R^2$ and $R^3$ is a hydrogen atom. The preferred metal salt is the sodium salt.

The metal salt complexes of this invention can be represented by the following formula which is presented for illustrative purposes only:

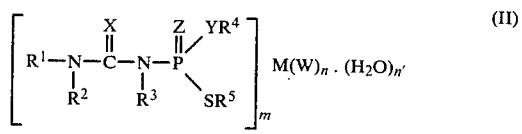  (II)

wherein $R^1$, $R^2$, $R^3$, $R^4$, $R^5$, X, and Y are as defined for Formula I;
M is a metal cation which can be selected from groups IIA, IIIA, IB, IIB, VIIB, and VIII of the periodic table;
W is an anion such as chloride, bromide, iodide, sulfate, bisulfate, phosphate, nitrate, perchlorate, carbonate, bicarbonate, hydroxide, acetate, oxalate, malate, citrate, and the like;
m is an integer of 1–2;
n is an integer of 1–2; and
n' is an integer of 0–4.

Among the compounds depicted by Formula II above, the preferred compounds are those wherein the metal cation is a transition metal such as copper, zinc, nickel, cobalt, tin, cadmium, or manganese; or an alkaline earth metal such as calcium or magnesium, and wherein the anion is chloride, bromide, nitrate, sulfate or hydroxide. The most preferred salts are those wherein the metal cation is copper, zinc, nickel, cobalt, tin, cadmium, or manganese, and the anion is hydroxide.

In Formulas I and II above, $R^2$ is preferably a hydrogen atom or a benzyl group or taken together with $R^1$ and the nitrogen atom to which they are attached, forms a piperidino group, and $R^3$ is a hydrogen atom.

The preferred compounds of this invention can be represented by the formula:

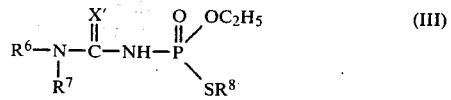  (III)

wherein $R^6$ is
(a) a hydrogen atom;
(b) a ($C_1$-$C_8$) alkyl group;
(c) a ($C_5$-$C_7$) cycloalkyl group;
(d) a phenyl, benzyl, or phenethyl group, preferably a benzyl or phenethyl group;
(e) a phenyl, benzyl, or phenethyl group, preferably a phenyl group, substituted with up to three, preferably up to two, methyl groups, methoxy groups, methylthio groups, dimethylamino groups, cyano groups, halogen atoms, especially chlorine, or trifluoromethyl groups;
(f) a pyridyl group optionally substituted with up to two ($C_1$-$C_4$) alkyl, preferably methyl, groups;
(g) a pyrazinyl group;

$R^7$ is a hydrogen atom or a benzyl group, provided that when $R^7$ is a hydrogen atom, $R^6$ is other than a substituted or unsubstituted phenyl group;

$R^6$ and $R^7$ taken together with the nitrogen atom to which they are attached, form a piperidino group;

$R^8$ is a n-propyl group, an isobutyl group or a sec-butyl group; and

X' is an oxygen or sulfur atom; and the agronomically acceptable metal salts and metal salt complexes thereof.

Among the preferred compounds, the most preferred are compounds wherein $R^6$ is
(a) a hydrogen atom,
(b) a ($C_1$-$C_4$) alkyl group,
(c) a cyclohexyl group,
(d) a benzyl or phenethyl group,
(e) a phenyl group substituted with up to two halogen atoms, preferably chlorine atoms;
(f) a pyridyl group substituted with a ($C_1$-$C_4$) alkyl, preferably methyl, group; or
(g) a pyrazinyl group;

$R^7$ is a hydrogen atom or a benzyl group, provided that when $R^7$ is a hydrogen atom, $R^6$ is other than a substituted phenyl group;

$R^6$ and $R^7$ taken together with the nitrogen atom to which they are attached, form a piperidino group;

$R^8$ is a n-propyl group or a sec-butyl group; and

X' is an oxygen or sulfur atom.

As used in the specification and claims, the term "substituted" when used to modify aralkyl, aryl, pyridyl, pyridylmethyl, pyridylethyl, or pyrazinyl groups, indicates that such groups are substituted with one or more substituents selected from the group consisting of ($C_1$-$C_4$) alkyl, ($C_1$-$C_4$) alkoxy, ($C_1$-$C_4$) alkylthio, ($C_1$-$C_4$) alkylsulfinyl, ($C_1$-$C_4$) alkylsulfonyl, di-($C_1$-$C_4$) alkylamino, ($C_1$-$C_4$) haloalkyl, ($C_1$-$C_4$) hydroxyalkyl, cyano, nitro, hydroxy, or halogen. The preferred substituents are methyl, methoxy, methylthio, dimethylamino, cyano, nitro, trifluoromethyl, and halogen, especially chlorine.

In the pyridyl and pyrazinyl rings, up to two substituents are preferred, while in the aralkyl and aryl groups, up to three substituents are preferred, up to two substituents being more preferred.

As used in the specification and claims, the terms alkyl, alkenyl, alkoxy, alkoxyalkyl, alkylthio, alkylthioalkyl, alkylsulfinyl, alkylsulfonyl, dialkylamino, haloalkyl, cyanoalkyl, hydroxyalkyl, aralkyl, and the like, are meant to include branched as well as straight chain groups.

Representative $R^1$ substituents include, for example, hydrogen, methyl, propyl, tert-butyl, dodecyl, cyclopropyl, cyclohexyl, cyclooctyl, phenyl, 3,5-dichlorophenyl, 4-chlorophenyl, 3,4-dichlorophenyl, 2,4-dichlorophenyl, 2,4,6-trichlorophenyl, 4 bromophenyl, 4-bromo-2-chlorophenyl, 4-fluorophenyl, 3,5-ditrifluoromethylphenyl, 2-chloro-4-methylphenyl, 2,4-dichloro-3,5-dimethylphenyl, 2-ethyl-4-methoxyphenyl, 4-butylphenyl, 4-methylthiophenyl, 3-methylsulfinylphenyl, 4-methylsulfonylphenyl, 5-methoxyphenyl, 2-ethoxyphenyl, 4-dimethylaminophenyl, 4-nitrophenyl, 2-cyanophenyl, 2-hydroxyphenyl, 2-hydroxymethylphenyl, benzyl, 3,5-dichlorobenzyl, 4-methylbenzyl, phenethyl, 4-methylthiophenethyl, α-methylbenzyl, naphthyl, 3,5-dichloronaphthyl, 3-trifluoromethylnaphthyl, 3-methylnaphthyl, 2-pyridyl, 3-pyridyl, 2-(5-chloropyridyl), 2-(3,5-dimethylpyridyl), 3-pyridylmethyl, 3-pyridylethyl, pyrazinyl, 2-(5-chloropyrazinyl), 2-(5-methylpyrazinyl), and the like.

Representative $R^2$ substituents include, for example, hydrogen, methyl, butyl, tert-butyl, nonyl, cyclobutyl, cyclohexyl, 2-ethoxyethyl, 4-butoxybutyl, 2-cyanoethyl, 4-cyanobutyl, 3-ethylthiopropyl, 2-butylthioethyl, allyl, phenyl, 3,5-dichlorophenyl, 2-methylphenyl, 4-cyanophenyl, 4-nitrophenyl, 4-methoxy-2-methylphenyl, benzyl, 3,5-ditrifluoromethylbenzyl, phenethyl, α-methylbenzyl, 3-phenylpropyl, 3,5-dichlorphenethyl, naphthyl, 4,6-dimethylnaphthyl, and the like.

Representative $R^3$ substituents include, for example, hydrogen, methyl, butyl, isobutyl, hexyl, cyclopentyl, cyclohexyl, allyl, 2-butenyl, phenyl, 2-methylphenyl, 3,5-dichlorophenyl, benzyl, 4-methylbenzyl, phenethyl, naphthyl, 3-methylnaphthyl, and the like.

Representative $R^4$ substituents include, for example, methyl, ethyl, propyl, isopropyl, butyl, sec-butyl, isobutyl, pentyl, hexyl, and the like.

Examples of the compounds embraced by this invention include:

aminothiocarbonyl O-ethyl S-(2-methylpropyl) phosphoramidothioate

O-butyl S-(1-methylpropyl)aminothiocarbonyl phosphoramidothioate

N-(N'-allyl, N'-ethyl)aminothiocarbonyl O-ethyl S-(1-methylpropyl) phosphoramidothioate N-(N'-2-ethoxyethyl, N'-hexyl)aminothiocarbonyl O-ethyl S-(1-methylpropyl) phosphoramidothioate N-cyclohexylaminothiocarbonyl O-ethyl S-(2-methylpropyl) phosphoramidodithioate N-allyl N-(N', N'-diphenyl)aminothiocarbonyl O-ethyl S-propyl phosphoramidothioate S,S-dipropyl N-[N'-ethyl N'-(1-naphthyl)]aminothiocarbonyl phosphoramidotrithioate N-[N'-(3,5-dichlorophenyl), N'-2-cyanoethyl]aminothiocarbonyl S,S-dipropyl phosphoramidodithioate N-[N'-cyclohexyl N'-(3-methyl-4-methylthiophenyl)-]aminothiocarbonyl O-ethyl S-(1-methylpropyl) phosphoramidothioate O-ethyl N-[N'-methyl N'-(4-methylsulfonylphenyl)-]aminothiocarbonyl S-(2-methylpropyl) phosphoramidothioate O-butyl S-(2-methylpropyl) N-(N'-2-methylthioethyl, N'phenyl)aminothiocarbonyl N-propyl phosphoramidothioate O-ethyl N-(4-methylbenzyl) S-(1-methylpropyl) N-phenethylaminothiocarbonyl phosphoramidothioate N-benzylaminothiocarbonyl O-butyl N-methyl S-(1-methylpropyl) phosphoramidothioate N-benzylaminothiocarbonyl O-ethyl S-(2-methylpropyl) N-phenyl phosphoramidothioate O-ethyl S-(2-methylpropyl) N-(2,3,4,5,6-pentachlorobenzyl) aminothiocarbonyl phosphoramidothioate N-(N', N'-dibenzyl)aminothiocarbonyl O-ethyl S-(2-methylpropyl) phosphoramidothioate O-ethyl S-(1-methylpropyl) N-(3-pyridylmethyl)aminothiocarbonyl phosphoramidothioate O-ethyl S-(1-methylpropyl) N-[3-(pyridyl)-1-ethyl]aminothiocarbonyl phosphoramidothioate N-[2-(5-chloropyridyl)]aminothiocarbonyl O-ethyl S-(1-methylpropyl) phosphoramidothioate N-[2-(6-chloropyrazinyl)]aminothiocarbonyl O-ethyl S-propyl phosphoramidothioate aminocarbonyl O-ethyl S-(2-methylpropyl) phosphoramidothioate O-ethyl N-methylaminocarbonyl S-(1-methylpropyl) phosphoramidothioate N-cyclopentylaminocarbonyl O-ethyl S-(1-methylpropyl) phosphoramidothioate N-[N'-(2-butenyl), N'-phenyl]aminocarbonyl O-methyl S-(1-methylpropyl) phosphoramidothioate N-[N'-butyl, N'-(3,5-ditrifluoromethylphenyl)-]aminocarbonyl O-ethyl S-propyl phosphoramidothioate N-[N'-benzyl, N'-(4-cyano-2-nitrophenyl)]aminocarbonyl O-ethyl S-(1-methylpropyl) phosphoramidothioate N-{N'-[1-(3,5-dichloronaphthyl), N'ethyl]}aminocarbonyl O-ethyl S-(2-methylpropyl) phosphoramidothioate N-cyclohexylaminocarbonyl N-3,5-dichlorophenyl O-ethyl S-propyl phosphoramidothioate N-[N'-(3,5-dichlorophenyl), N'-(4-methylphenyl)-]aminocarbonyl O-ethyl S-(1-methylpropyl) phosphoramidothioate O-ethyl N-(2-hydroxyphenyl)aminocarbonyl S-(1-methylpropyl) phosphoramidothioate O-ethyl N-(2-hydroxymethyl)aminocarbonyl S-(1-methylpropyl) phosphoramidothioate N-benzylaminocarbonyl N-cyclohexyl O-methylethyl S-(1-methylpropyl) phosphoramidothioate N-benzyl O-ethyl S-(2-methylpropyl) N-(2-phenethyl)aminocarbonyl phosphoramidothioate N-(N',N'-dibenzyl)aminocarbonyl O-ethyl S-(2-methylpropyl) phosphoramidothioate O-ethyl S-(1-methylpropyl) N-(2-pyridyl)aminocarbonyl phosphoramidothioate O-ethyl S-(2-methylpropyl) N-(3-pyridylmethyl)aminocarbonyl phosphoramidothioate N-(5-bromo-2-pyrazinyl)aminocarbonyl O-ethyl S-(1-methylpropyl) phosphoramidothioate O-ethyl S-(2-methylpropyl) N-morpholinocarbonyl phosphoramidothioate and the agronomically acceptable metal salts and metal salt complexes thereof, and the like.

The phosphoramidates of this invention are prepared by various methods. One method involves contacting ammonia or an appropriate alkyl, aralkyl, aromatic or heterocyclic amine with an appropriate phosphoroisothiocyanate or isocyanate. This reaction can be represented by the following equation:

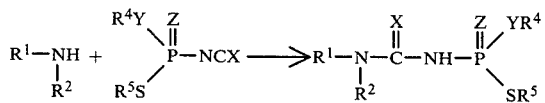

wherein $R^1$, $R^2$, $R^4$, $R^5$, X, Y, and Z are as defined for Formula I.

The reaction is generally carried out in the presence of an aprotic solvent such as glyme, acetone, acetonitrile, ethyl acetate, butyl acetate, diethyl ether, or mixtures thereof, at a temperature range of about 15° C. to about 120° C., preferably at about 25° C. to about 45° C. A substantially equimolar ratio of reactants is preferred but an excess of phosphoroisothiocyanate or isocyanate can be used. The desired product can be separated from the reaction mixture by conventional means, such as fractional crystallization, chromatography, extraction or the like.

Another method for preparing compounds within the scope of this invention involves contacting ammonia or an appropriate alkyl, aralkyl, aromatic, or heterocyclic amine with an appropriate chlorocarbonyl or chlorothiocarbonyl phosphoramidate. This reaction can be represented by the following equation:

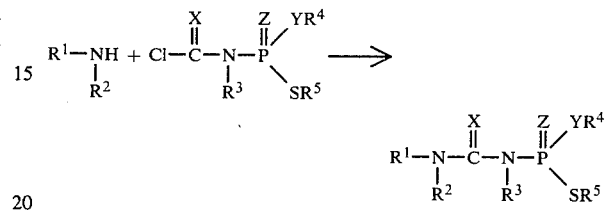

wherein $R^1$, $R^2$, $R^3$, $R^4$, $R^5$, X, Y, and Z are as defined for Formula I, with the exception that $R^3$ may not be hydrogen.

This reaction is generally carried out in the presence of an aprotic solvent such as glyme, acetone, acetonitrile, ethyl acetate, butyl acetate, diethyl ether, or mixtures thereof, at a temperature range of about 15° C. to about 120° C., preferably at about 25° C. to about 45° C. An acid acceptor such as a tertiary amine can be employed as a scavenger in this preparation. Representative acid acceptors include pyridine, trimethylamine, triethylamine, and the like. However, an excess of the amine reactant can also serve as the acid acceptor. Generally, a substantially equimolar ratio of reactants is preferred, but an excess of two or more moles of amine can be employed if the amine is intended to serve the dual function of reactant and acid acceptor. The desired product can be separated from the reaction mixture by conventional means.

A third method of preparing compounds of this invention involves contacting an appropriate phosphoramidate with an appropriate isocyanate or isothiocyanate. This reaction can be represented by the following equation:

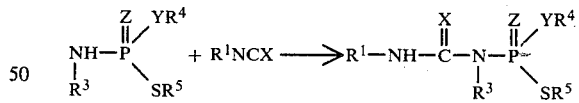

wherein $R^1$, $R^3$, $R^4$, $R^5$, X, Y, and Z are as defined for Formula I.

The reaction is generally carried out in the presence of an aprotic solvent such as glyme, acetone, acetonitrile, ethyl acetate, butyl acetate, diethyl ether, or mixtures thereof, at a temperature range of about 20° C. to about 60° C., room temperature being preferred. A substantially equimolar ratio of reactants is preferred. The desired product can be separated from the reaction mixture by conventional means.

The metal salts of this invention are prepared by (1) adding an alkali or alkaline earth metal hydroxide or hydride to a suspension of the phosphoramidate in a suitable solvent, (2) stirring the mixture until a solution forms and (3) freeze drying the solution, or in the alternative, (4) concentrating the solution in vacuo at room temperature, and drying the residue in a vacuum oven at room temperature.

The metal salt complexes are prepared by (1) reacting, in an aqueous or alcoholic medium, a phosphoramidate of this invention with a metal salt selected from group IIA, IIIA, IB, IIB, VIIB, or VIII or the periodic table, (2) filtering off the precipitate which forms, and (3) washing and drying the precipitate to give the product.

All of the starting materials used in the preparation of the compounds of this invention are known compounds or are readily prepared by methods available to those skilled in the art.

By way of demonstration, the following examples are offered to illustrate this invention and are not to be construed as limitations thereof.

EXAMPLE 7—Preparation of N-cyclohexylaminocarbonyl O-ethyl S-(1-methylpropyl) phosphoramidothioate To a solution of 0.99 g. (0.01 mole) of cyclohexylamine in five ml. of glyme is added 2.23 g. (0.01 mole) of O-ethyl S-(1-methylpropyl) phosphoroisocyanatothioate (exothermic reaction). The suspension which forms is allowed to stand at room temperature for one hour and is then poured into 20 ml. of ether. The suspension is vacuum filtered and the filtrate is allowed to stand at room temperature for 18 hours after which it is concentrated under a stream of nitrogen. The residue semisolid is slurried in 50 ml. of hexane, filtered and dried, to afford 0.4 g. (12.5%) of product.

EXAMPLE 11—Preparation of N-(N',N'-dibenzyl)aminothiocarbonyl O-ethyl S-(1-methylpropyl) phosphoramidothioate To a solution of 0.99 g. (0.005 mole) of dibenzylamine in five ml. of glyme is added 1.12 g. (0.005 mole) of O-ethyl S-(1-methylpropyl) phosphoroisocyanatothioate (exothermic reaction). The solution is allowed to stand at room temperature overnight and the fine suspension which forms is vacuum filtered. The filtrate is dissolved in 50 ml. of ether, washed with water, dried over magnesium sulfate, and concentrated under a stream of nitrogen to afford 1.5 g. (71%) of colorless oil.

EXAMPLE 13—Preparation of N-benzylaminocarbonyl O-ethyl S-(1-methylpropyl) phosphoramidothioate To a solution of 1.07 g. (0.01 mole) of benzylamine in five ml. of glyme is added 2.23 g. (0.01 mole) of O-ethyl S-(1-methylpropyl) phosphoroisocyanatothioate (exothermic reaction). The suspension which forms is allowed to stand at room temperature for two hours and then vacuum filtered. The filter cake is washed with ether and dried to afford 1.5 g. (46%) of product, m.p. 117°–120° C. Recrystallization from methylcyclohexane gives 0.7 g. (23%) of product.

EXAMPLE 16—Preparation of N-[N'-benzyl, N'-(3,5-dichlorophenyl)]aminocarbonyl O-ethyl S-(1-methylpropyl) phosphoramidothioate To a solution of 1.26 g. (0.005 mole) of N-benzyl-3,5-dichloroaniline in 50 ml. of glyme is added 1.12 g. (0.005 mole) of O-ethyl S-(1-methylpropyl) phosphoroisocyanatothioate. The solution is allowed to stand at room temperature for three days and the suspension which forms is filtered. The filter cake is washed with hexane and dried to yield 0.3 g. (13%) of product.

EXAMPLE 17—Preparation of O-ethyl S-(1-methylpropyl) N-[2-(5-methylpyridyl)]aminothiocarbonyl phosphoramidothioate To a solution of 1.08 g. (0.01 mole) of 2-amino-5-methylpyridine in 50 ml. of glyme is added 2.39 g. (0.01 mole) of O-ethyl S-(1-methylpropyl) phosphoroisothiocyanatothioate (exothermic reaction). The solution is allowed to stand at room temperature for two hours and then poured into an excess of water. The suspension which forms is vacuum filtered and the filter cake is slurried in 50 ml. of hexane. The slurry is vacuum filtered and the filter cake dried to afford 2.2 g. (65%) of product.

EXAMPLE 18—Preparation of O-ethyl S-propyl N-pyrazinylaminothiocarbonyl phosphoramidothioate To a fine suspension of 0.95 g. (0.01 mole) of aminopyrazine in a five ml. of acetonitrile is added 2.25 g. (0.01 mole) of O-ethyl S-propyl phosphoroisothiocyanatothioate. The solution which forms is allowed to stand at room temperature for five days and then poured into an excess of water. The suspension is vacuum filtered and the filter cake is washed with ether and dried to afford 0.5 g. (15%) of product.

TABLE I

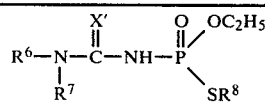

| Compound Number | X' | R⁶ | R⁷ | R⁸ | M.P., °C. | ELEMENTAL ANALYSIS Calculated (Found) | | | | |
|---|---|---|---|---|---|---|---|---|---|---|
| | | | | | | %C | %H | %N | %P | %S |
| 1 | S | H | H | $C_4H_9{}^s$ | 105–107 | 32.34 (32.80) | 6.86 (6.69) | 11.03 (10.93) | 12.05 (12.08) | — — |
| 2 | O | H | H | $C_4H_9{}^s$ | 177–180 dec. | 34.84 (34.99) | 7.32 (7.13) | 11.58 (11.66) | — — | — — |
| 3 | O | CH₃ | H | $C_4H_9{}^s$ | 135.5–138 | 37.8 (37.4) | 7.5 (7.3) | 11.0 (11.0) | — — | — — |
| 4 | O | C₃H₇n | H | $C_4H_9{}^s$ | 72–76 | 42.6 (41.2) | 8.2 (8.3) | 9.9 (9.0) | — — | — — |
| 5 | S | C₄H₉ | H | $C_4H_9{}^s$ | oil | 42.76 (42.28) | 8.17 (8.08) | 8.62 (8.97) | 9.72 (9.91) | — — |
| 6 | O | C₄H₉-t | H | $C_4H_9{}^s$ | oil | 44.6 (48.4) | 8.1 (9.2) | 10.6 (10.7) | — — | — — |

TABLE I-continued $$R^6-\underset{\underset{R^7}{|}}{N}-\overset{\overset{X'}{\|}}{C}-NH-\overset{\overset{O}{\|}}{P}\overset{OC_2H_5}{\underset{SR^8}{\diagup}}$$

| Compound Number | X' | R⁶ | R⁷ | R⁸ | M.P., °C. | %C | %H | %N | %P | %S |
|---|---|---|---|---|---|---|---|---|---|---|
| 7 | O | cyclo-C₆H₁₁ | H | C₄H₉ˢ | 100–104 dec. | 47.60 (48.43) | 8.56 (8.44) | 8.76 (8.69) | 9.71 (9.61) | — |
| 8 | O | C₄H₉ᵗ | H | C₄H₉ˢ | 83–86 | 44.6 (44.1) | 8.1 (8.5) | 9.4 (9.6) | — | — |
| 9 | S | cyclo-C₆H₁₁ | H | C₄H₉ˢ | oil | 46.98 (46.13) | 8.43 (8.04) | 7.46 (8.28) | — | — |
| 10 | O | C₆H₅CH₂ | C₆H₅CH₂ | C₄H₉ˢ | oil | 59.98 (58.65) | 6.95 (6.98) | 6.66 (6.45) | 7.37 (7.17) | — |
| 11 | S | C₆H₅CH₂ | C₆H₅CH₂ | C₄H₉ˢ | oil | 57.77 (57.53) | 6.70 (6.73) | 6.52 (6.67) | 7.10 (7.12) | — |
| 12 | S | C₆H₅CH₂ | H | C₄H₉ˢ | oil | 49.52 (48.53) | 6.87 (6.69) | 7.29 (8.02) | 9.03 (8.94) | — |
| 13 | O | C₆H₅CH₂ | H | C₄H₉ˢ | 120–122 | 50.94 (50.89) | 7.04 (7.02) | 8.65 (8.48) | 9.53 (9.38) | — |
| 14 | S | C₆H₅CH₂CH₂ | H | C₄H₉ˢ | oil | 50.75 (49.96) | 7.15 (6.99) | 7.38 (7.77) | — | — |
| 15 | O | C₆H₅CH₂CH₂ | H | C₄H₉ˢ | 95–98 dec. | 52.07 (52.31) | 7.27 (7.32) | 7.96 (8.14) | 9.00 (8.99) | — |
| 16 | O | C₆H₃Cl₂-3,5 | C₆H₅CH₂ | C₄H₉ˢ | 118–120 | 50.39 (50.53) | 5.17 (5.30) | 5.96 (5.89) | 6.51 (6.52) | — |
| 17 | S | 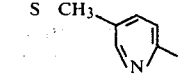 | H | C₄H₉ˢ | 118–120 | 44.78 (44.94) | 6.08 (6.38) | 12.07 (12.09) | 8.83 (8.92) | — |
| 18 | S | 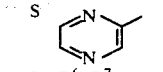 | H | C₃H₇ | 106–107 dec. | 37.49 (37.44) | 5.35 (5.38) | 17.49 (17.31) | 9.67 (9.66) | — |
| 19 | O | R⁶, R⁷ = ₊CH₂₋₅ | | C₄H₉ˢ | 69–71 | 46.8 (47.1) | 8.2 (8.5) | 9.1 (9.2) | — | — |

ˢ = secondary butyl
ᵗ = tertiary butyl

The present compounds and the metal salts and metal salt complexes thereof (hereinafter collectively referred to as compounds) are biocidally active, particularly against nematodes, e.g. the southern root knot nematode, *Meloidogyne incognita*. In addition to possessing utility as nematocides, compounds of this invention are also useful as arthropodicides, especially as insecticides or acaricides, and as anthelmintics.

For use as nematocides, the compounds of this invention are applied in any variety of formulations. For example, they can be applied as wettable powders, emulsifiable concentrates, dusts, granular formulations or flowable emulsifiable concentrates. Preferably, the compounds are extended with an agronomically acceptable liquid or solid carrier and, when desired, suitable surfactants are likewise incorporated. Surfactants commonly used in the art can be found in the John W. McCutcheon, Inc. publication "Detergents and Emulsifiers Annual".

The compounds can be taken up on or mixed with a finely particled solid carrier, as for example, clays, inorganic silicates, carbonates, and silicas. Organic carriers can also be employed. Dust concentrates can be made wherein the compound is present in the range of about 20 to about 80%. For ultimate applications, these concentrates are normally extended with additional solid to give an active ingredient content of from about 1 to about 20%. Granular formulations are made using a granular or pelletized form of carrier, such as granular clays, vermiculite, charcoal or corn cobs, and can contain the active ingredient in from about 1 to about 25% by weight.

Wettable powder formulations are made by incorporating the compounds of this invention in an inert, finely divided solid carrier along with a surfactant which can be one or more emulsifying, wetting, dispersing or spreading agents or a blend of these. The compound is usually present in the range of about 10 to about 80% by weight and surfactants in from about 0.5 to about 10% by weight.

One convenient method for preparing a solid formulation is to impregnate toxicant onto the solid carrier by means of a volatile solvent, such as acetone. In this manner, adjuvants such as activators, adhesives, plant nutrients, synergists and various surfactants can also be incorporated.

Emulsifiable concentrate formulations can be prepared by dissolving a compound of this invention in an agronomically acceptable organic solvent and adding a solvent-soluble emulsifying agent. Suitable solvents are usually water-immiscible and can be hydrocarbon, chlorinated hydrocarbon, ketone, ester, alcohol and amide organic solvents. Mixtures of solvents are commonly employed. The surfactants useful as emulsifying agents can constitute about 0.5 to about 10% by weight of emulsifiable concentrate and can be anionic, cationic or non-ionic in character. The concentration of the active ingredients can vary from about 10 to about 80%, preferably in the range of about 25 to 50%.

The compounds of this invention are applied in an effective amount sufficient to exert the desired nematocidal effect according to techniques well known in the art. Usually, this will involve the application of the active compounds directly to the pests or loci to be protected from attack by such pests in an effective amount when incorporated in an agronomically acceptable carrier.

The application rate will, of course, vary depending upon the method of application, the purposes for such application, the compound being utilized, the frequency of dissemination, the type and quantity of nematodes, climatic conditions, and the like.

As nematocidal compositions, the compounds of this invention may be applied in liquid form but are preferably applied as a granular formulation, by broadcasting, side-dressing, introduction into the seed furrow or by soil incorporation. The compositions can also be added to transplant water or employed as dips or soaks for vegetative parts employed in propagation, such as seeds, tubers, roots, seedlings, etc., so as to disinfect and/or provide residual protection from nematodes. The application rate can be from about 1 to about 50 pounds per acre; however, higher rates can also be used. The preferred rate is from about 1 to about 25 pounds per acre. For soil incorporation, the compounds of this invention can be mixed with the soil at a rate of about 2 to about 100 p.p.m. of active ingredient.

The compounds of this invention can be utilized as the sole biocidal agents or they can be employed in conjunction with other nematocides, bactericides, fungicides, herbicides, insecticides, acaricides, and comparable pesticides.

Many variations of this invention are possible without departing from the spirit or scope thereof.

We claim:

1. A method of controlling nematodes which comprises applying directly to the nematodes or to the loci to be freed of or protected from attack by such nematodes, a nematocidally effective amount of a compound of the formula $$R^6-\underset{R^7}{\underset{|}{N}}-\overset{X'}{\overset{\|}{C}}-NH-\overset{O}{\overset{\|}{P}}\underset{SR^8}{\overset{OC_2H_5}{\diagup}}$$

wherein $R^6$ is
 (a) a hydrogen atom,
 (b) a ($C_1$-$C_8$) alkyl group,
 (c) a ($C_5$-$C_7$) cycloalkyl group;
$R^7$ is a hydrogen atom;
$R^6$ and $R^7$ taken together with the nitrogen atom to which they are attached, form a piperidino group optionally substituted with up to two ($C_1$-$C_4$) alkyl groups;
$R^8$ is a n-propyl group, an isobutyl group or a sec-butyl group; and
$X'$ is an oxygen or sulfur atom.

2. A method of controlling nematodes which comprises applying directly to the nematodes, a nematocidally effective amount of a composition comprising a compound of the formula $$R^6-\underset{R^7}{\underset{|}{N}}-\overset{X'}{\overset{\|}{C}}-NH-\overset{O}{\overset{\|}{P}}\underset{SR^8}{\overset{OC_2H_5}{\diagup}}$$

wherein $R^6$ is
 (a) a hydrogen atom,
 (b) a ($C_1$-$C_8$) alkyl group,
 (c) a ($C_5$-$C_7$) cycloalkyl group;
$R^7$ is a hydrogen atom;
$R^6$ and $R^7$ taken together with the nitrogen atom to which they are attached, form a piperidino group optionally substituted with up to two ($C_1$-$C_4$) alkyl groups;
$R^8$ is a n-propyl group, an isobutyl group or a sec-butyl group; and
$X'$ is an oxygen or sulfur atom
and an agronomically acceptable carrier.

3. A compound having the formula:

$$\text{cyclohexyl}-NH-\overset{O}{\overset{\|}{C}}-NH-\overset{O}{\overset{\|}{P}}\underset{SC_4H_9\text{-sec}}{\overset{OC_2H_5}{\diagup}}$$

* * * * *